United States Patent [19]

Wright

[11] Patent Number: 4,662,869

[45] Date of Patent: May 5, 1987

[54] PRECISION INTRAOCULAR APPARATUS

[76] Inventor: Kenneth W. Wright, 1375 Pasqualito Dr., San Marino, Calif. 91108

[21] Appl. No.: 672,930

[22] Filed: Nov. 19, 1984

[51] Int. Cl.$^4$ .............................................. A61B 17/20
[52] U.S. Cl. .................................... 604/22; 128/305; 128/752
[58] Field of Search ...................... 128/303.14, 303.17, 128/752–755, 305, 311; 604/22, 35, 319, 264, 267, 275

[56] References Cited

U.S. PATENT DOCUMENTS

| | | | |
|---|---|---|---|
| 3,776,238 | 12/1973 | Peyman et al. | 128/305 |
| 3,815,604 | 6/1974 | O'Malley et al. | 128/305 |
| 3,882,872 | 5/1975 | Douvas et al. | 128/305 |
| 3,884,237 | 5/1975 | O'Malley et al. | 128/303.14 |
| 3,884,238 | 5/1975 | O'Malley et al. | 128/305 |
| 4,108,182 | 8/1978 | Hartman et al. | 128/305 |

OTHER PUBLICATIONS

Peyman G., and Dodich N., "Experimental Vitrectomy", *Arch Ophthal*, vol. 86, Nov. 1971, pp. 548–551.

Primary Examiner—C. Fred Rosenbaum
Assistant Examiner—Jerome R. Smith, Jr.
Attorney, Agent, or Firm—Kendrick, Netter & Bennett

[57] ABSTRACT

A precision intraocular surgical tool for removal or severing and removal of tissue from the eyeball of a patient includes a first tube of very small diameter having a port near one end, with the port including a tissue-shearing portion and, towards the closed end of the tube, a portion of substantially smaller size than the tissue-shearing portion, and a second tube concentric with the first tube. The first and second tubes fit snugly together, and one of the tubes is slidable with respect to the other. The end of the second tube adjacent to the port has a sharp cutting edge portion, and may also include a second smooth portion. The tool includes a mechanism for drawing tissue into the port for moving one of the tubes so that the sharp cutting edge portion can cross the port and cut tissue sucked into the port or, alternatively, so that the opening in the port can be restricted to the smaller-sized portion for aspirating tissue from the eyeball of a patient without cutting such tissue.

6 Claims, 11 Drawing Figures

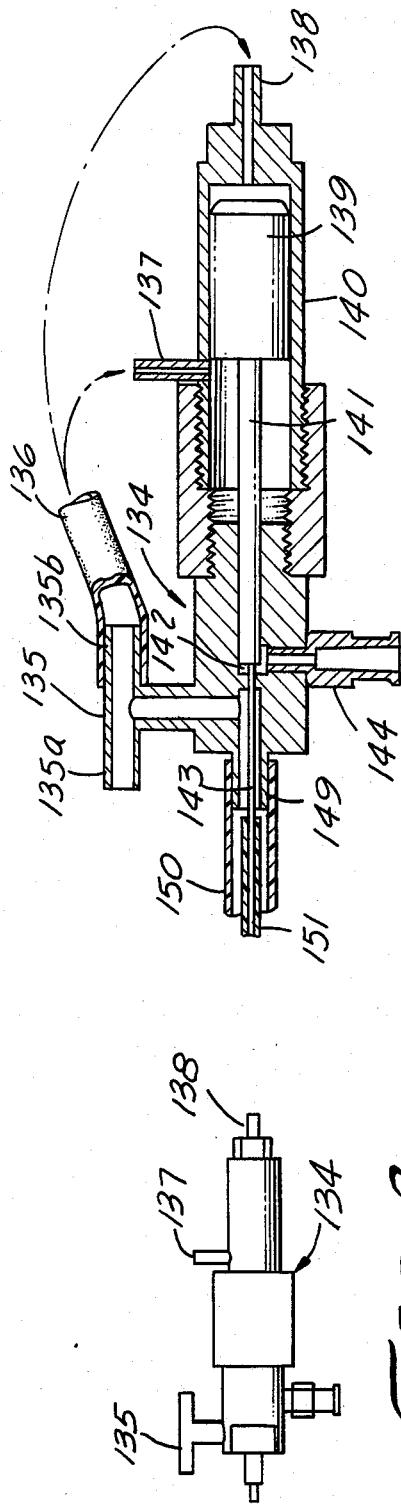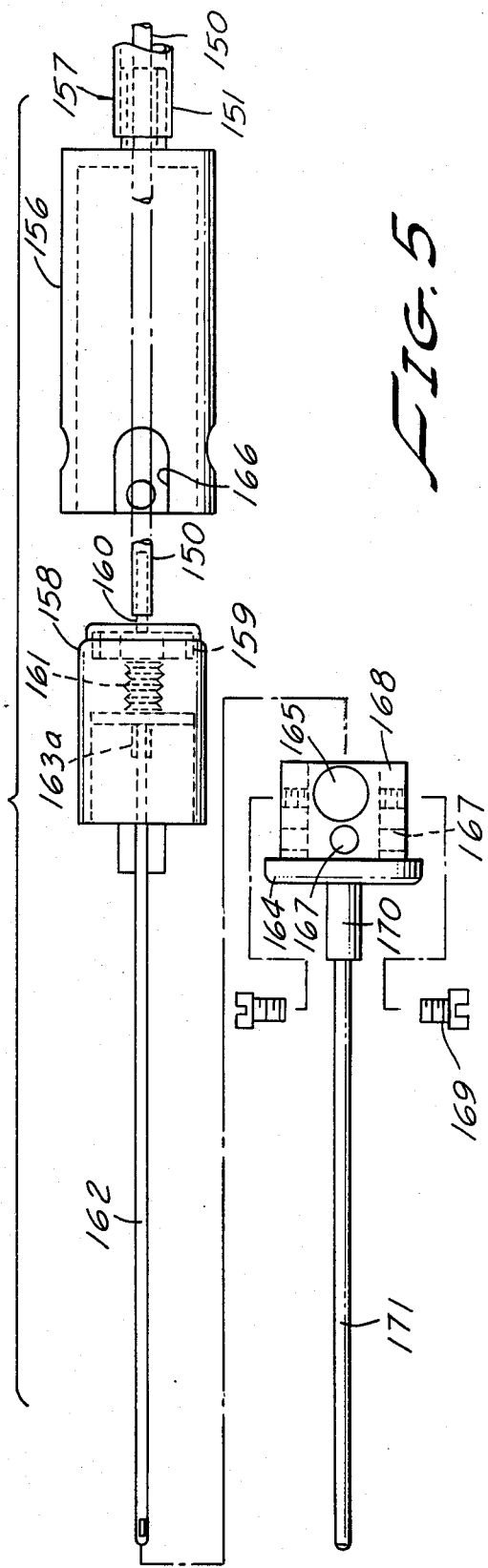

PRECISION INTRAOCULAR APPARATUS

This invention relates to an apparatus for use in effecting intricate surgery such as performed by an ophthalmic surgeon. Such surgical apparatus are disclosed in U.S. Pat. Nos. 3,884,238 and 3,815,604. We incorporate herein by reference the entire disclosures of these patents. These devices, though commercially successful, exhibit some drawbacks. For example, these devices do not permit precise, pinpoint aspiration or withdrawal of tissue from the human eye, particularly where a surgeon wishes to withdraw such tissue without cutting or severing such tissue in the process.

This invention provides an intraocular surgical apparatus that permits both precise, pinpoint aspiration of eye tissue without cutting any tissue, and the aspiration/cutting function of the surgical apparatus disclosed in the patents identified above. This new apparatus comprises a first tube of very small diameter having a port near one end. This port includes a tissue-shearing portion and, toward the closed end of the tube, a portion of substantially smaller size than the tissue-shearing portion. The smaller-sized portion is especially useful in precise, pinpoint aspiration of eye tissue without disturbing or cutting surrounding tissues.

The apparatus also includes a second tube concentric with the first tube. The first and second tubes fit snugly together, with one of the tubes being slidable with respect to the other tube. The end of the second tube adjacent the port in the first tube has a sharp cutting edge portion and may, but need not include a second, smoother portion. Either the first tube or the second tube may be rotated to bring the second, smoother portion into the port, or into a path that passes across the port. The device also includes means for reciprocating one of the tubes with respect to the other. As a result, the sharp, cutting edge portion can cross the port and shear tissues sucked into the port or, alternatively, the size of the opening in the port can be varied and restricted, as desired, to the smaller-sized portion for precise, pinpoint withdrawal or aspiration of eye tissue. Rotating the smoother portion of the second tube into the port minimizes the risk of inadvertently cutting any tissue, particularly where the opening in the port is restricted to its smaller-sized portion.

The new surgical tool also includes, in preferred embodiments, a source of vacuum, and means for connecting the source of vacuum to the inner one of said tubes for drawing eye tissue into the first tube through the port in the tube.

In addition to the features described herein, the apparatus of this invention can include features disclosed in the two above-identified patents. By this reference, we incorporate here the entire disclosures of these patents.

The new intraocular surgical apparatus can be better understood by reference to the drawings, in which:

FIG. 3 is a side view of the pneumatic control device that forms part of the device illustrated in FIG. 1;

FIG. 4 is a sectional view of the control device shown in FIG. 3;

FIG. 5 is an exploded view of a pull-type surgical apparatus of this invention;

Figure 1:
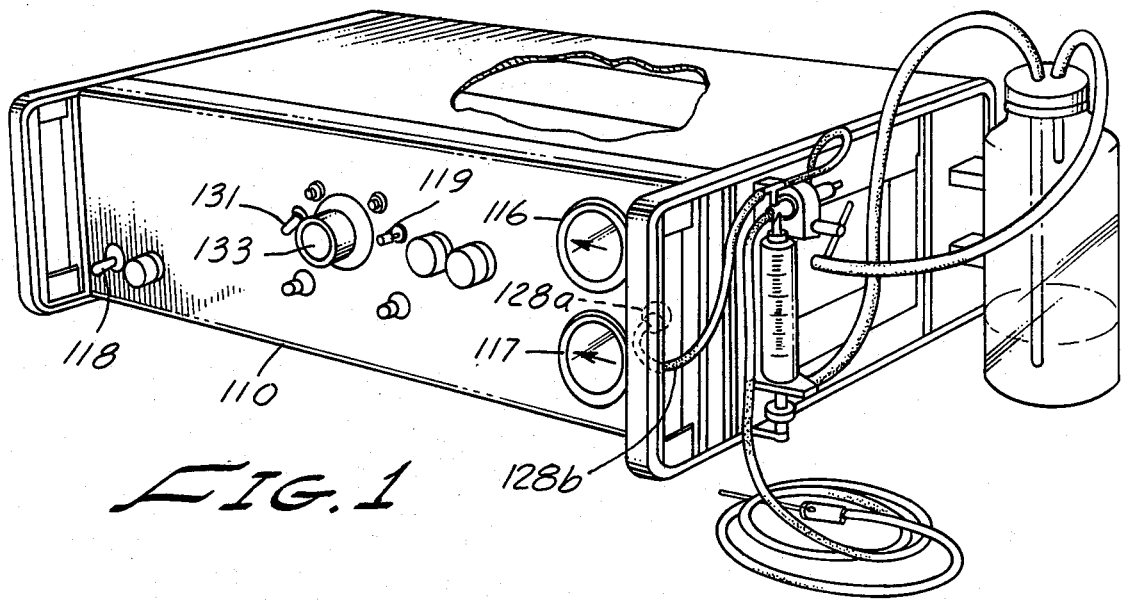
FIG. 1 is a perspective view of a device including a preferred embodiment of the new surgical apparatus.
Figure 2:
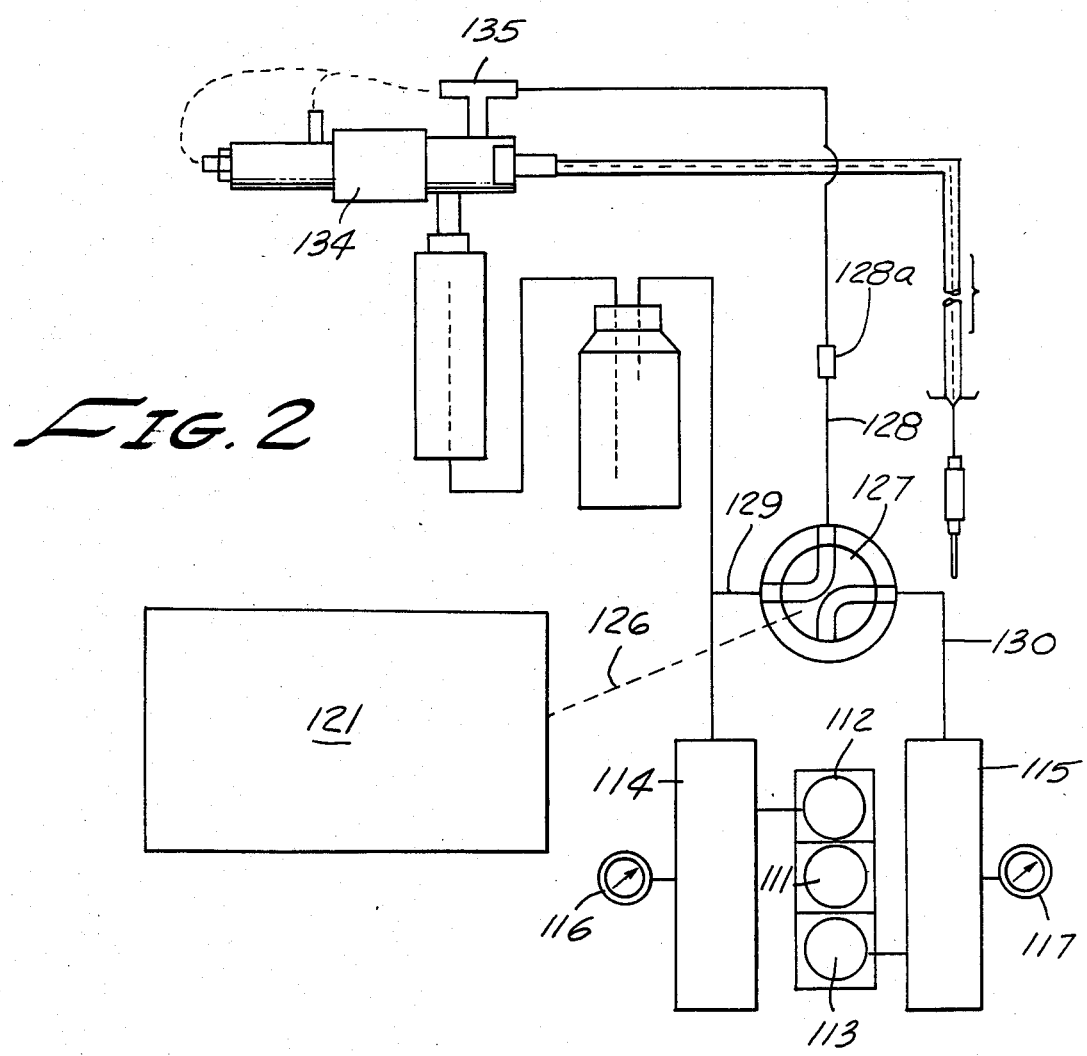
FIG. 2 is a schematic diagram showing controls for the device depicted in FIG. 1.

Referring to the drawings in detail, cabinet 110 houses various controls such as shown in FIG. 2. Motor 111, which is mechanically connected to vacuum pump 112 and air pressure pump 113, is housed in cabinet 10, together with pumps 112 and 113, which are connected by suitable tubes to tanks 114 and 115, respectively. Vacuum gauge 116 is linked by a suitable tube to tank 114 and pressure gauge 117 is connected by a suitable tube to pressure tank 115. These gauges are located on the front panel of cabinet 110 so that the dials thereon are visible to the operator. Motor 111 is connected to a suitable source of electric power, and to switch 118 as provided on the panel of cabinet 110 for turning the motor on and off. Auxiliary switch 119 is provided between the power line and a DC power supply which converts alternating current supplied thereto to direct current for energizing a multi-vibrator and flip-flops, as shown in FIGS. 1 and 2 of U.S. Pat. No. 3,815,604, and as described at column 5 of that patent.

Multi-vibrator/flip-flop array 121 includes a multi-vibrator for triggering the flip-flop to produce an output designated as a mode A signal, which may be supplied to a summing gate through a switch when it is desired to actuate the solenoid and deliver a signal to valve 127 on path 126. In mode A, valve 127 is actuated to connect the output line 128 for equal intervals to vacuum line 129 and pressure line 130. Multi-vibrator/flip-flop array 121 is shifted to connect the output of one of the flip-flops therein to another. The apparatus is then operated in mode B and the waveform of this mode is supplied to the summing gate and to the solenoid for controlling valve 127. In mode B, valve 127 is operated so that it connects the output line 128 to the vacuum or suction line 129 for an interval approximately three times as long as the interval during which this line 128 is connected to pressure line 130. The mode B signal may be used to connect output line 128 to pressure line 130 for a longer interval than the interval during which it is connected to the vacuum line, if desired.

The desired mode may be selected by operating switch 131. This switch appears on the front panel of cabinet 110. Cabinet 110 also houses a variable resistor which may be varied by a conventional foot control for controlling the frequency of the pulses in modes A and B. The multi-vibrator within multi-vibrator/flip-flop array 121 supplies electrical pulses for triggering the flip-flops and thus controls the frequency of the pulses produced by the flip-flop. The variable resistor may also be provided with a foot control although it is shown as being controlled by knob 133a on the front panel of cabinet 110.

Line 128 is connected to fitting 128a attached to the front panel of cabinet 110. This fitting is of the quick disconnect Luer type so that the line or tube 128b provided between it and the vacuum control device 134, may be readily disconnected therefrom. Device 134, shown in detail in FIG. 4, is provided with a T-connection 135 having two arms 135a and 135b. Line 128b is connected to arm 135a. Arm 135b is connected to line 136 which may be connected either to inlet 137 or inlet 138 of the control device 134 for purposes described below. Control device 134 includes piston 139 made of plastic that is slidable in cylinder 140. Ports 137 and 138 lead into this cylinder, with port 137 leading in below piston 139, and port 138 leading in at the top end thereof.

Piston rod 141, also made of plastic, is attached to piston 139, and extends into cavity 142, into which small tube 143 also extends. This end of tube 143 is carefully lapped and polished and provides a seat for the end of rod 141. The lapped and polished end of tube 143 is alternately opened and closed by the end of piston rod 141 as piston 139 moves back and forth during operation of the device. The Luer-type fitting 144 is attached to control device 134 and provides a connection between small cavity 142 and the cylinder 145 which may be of 5 cc. capacity calibrated in one-tenth cc. increments to measure the material removed from the eye of a patient. Standpipe 145a in cylinder 145 is connected by line 146 to the top of waste overflow bottle 147. Bottle 147 is also connected to vacuum line 148 so that vacuum is provided therein.

Vacuum control device 134 is also provided with an extension neck 149 and the small tube 143 which may have an outer diameter of 0.6 millimeters, and is concentric with the extension neck 149. Tube 143 extends outwardly beyond extension 149 so that a small debris tube 150 is attached to the projecting part of small tube 143. Tube 150 is positioned inside tube 151, which is in turn attached to projection 149 on device 134. Tubes 150 and 151 are attached to a cutting and debris extracting device as indicated at 152, which may either of the types shown in FIG. 5 or of the type shown in FIGS. 6 and 7.

The pull-cut device shown in FIG. 5 includes housing 156, which also functions as a handle, and which includes tubular projection 157 at one end thereof. Plastic tube 151 is attached to projection 157 so that alternate air and suction pulses can be provided to the inside of this housing to operate piston 158. Piston 158 is slidably positioned in housing 156. Piston 158 can be made of fluorcarbon plastic. One end of piston 158 is indented to receive nut 159, which engages the enlarged threaded portion 161 of the debris tube. Portion 160 of the debris tube extends out of the piston and is inserted into line 150 through which debris is exhausted from small stainless tube 162.

Piston 158 is provided with a flag which projects from one end thereof and slides in a slot provided in cap 164. This flag keeps the piston from rotating with respect to cap 164. Cap 164 is provided with a knob 165 received by slot 166 on housing 156 when the cap is attached to the housing. Thus, flag 163 orients piston 158 with respect to cap 164 and knob 165 serves to orient cap 164 with respect to housing 156. Cap 164 is provided with four radially extending holes 167 through depth to be aligned with corresponding holes in housing 156 to provide venting the inside of the housing during operation of the apparatus. By providing four such holes, it is not possible for the operator of this device to cover all holes simultaneously during use of the device so as to interfere with its operation. Suitable threaded holes 168 are provided in cap 164, and screws are threaded into these holes through suitable apertures in housing 156 when the cap is assembled with the housing.

Figure 8:
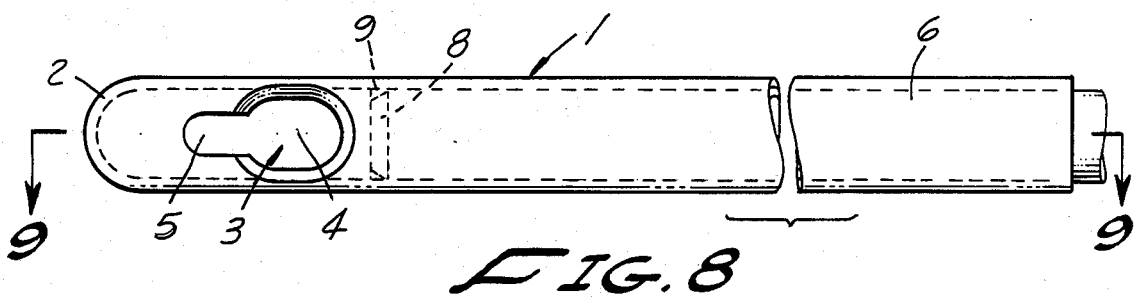
FIG. 8 is a plan view of a preferred embodiment of the new surgical apparatus.
Figure 9:
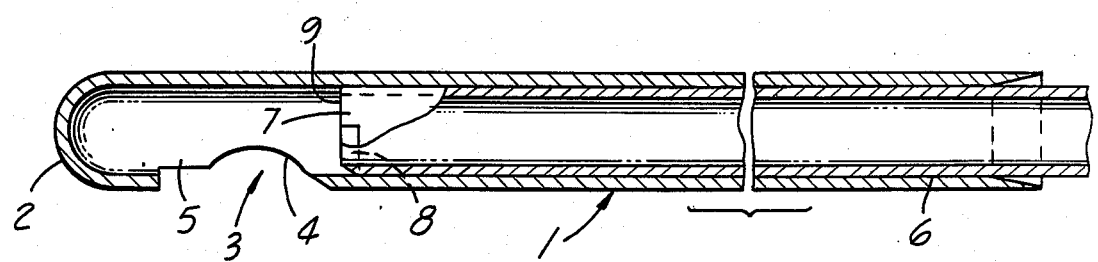
FIG. 9 is a side elevation, cross-sectional view of the apparatus shown in FIG. 8, taken on line 9—9 in FIG. 8.

Tubular extension 170 is provided on the outside end of cap 164 for receiving stainless steel tube 171. The outer end of tube or sleeve 171 is tapered and sharpened, in part, as shown in FIGS. 8 and 9. The sharp cutting edge of sleeve 171 provides shearing action with the sides of the port provided in inner sleeve 162. The shearing action takes place as inner sleeve 162 moves inwardly with respect to outer sleeve 171 by means of piston 158.

Suction is supplied to inner sleeve 161 through tube 151 so that debris cut from the inside of an eye is exhausted through the port formed in sleeve 162 and through the tube in sleeve 171 in tube 150.

Figure 6:
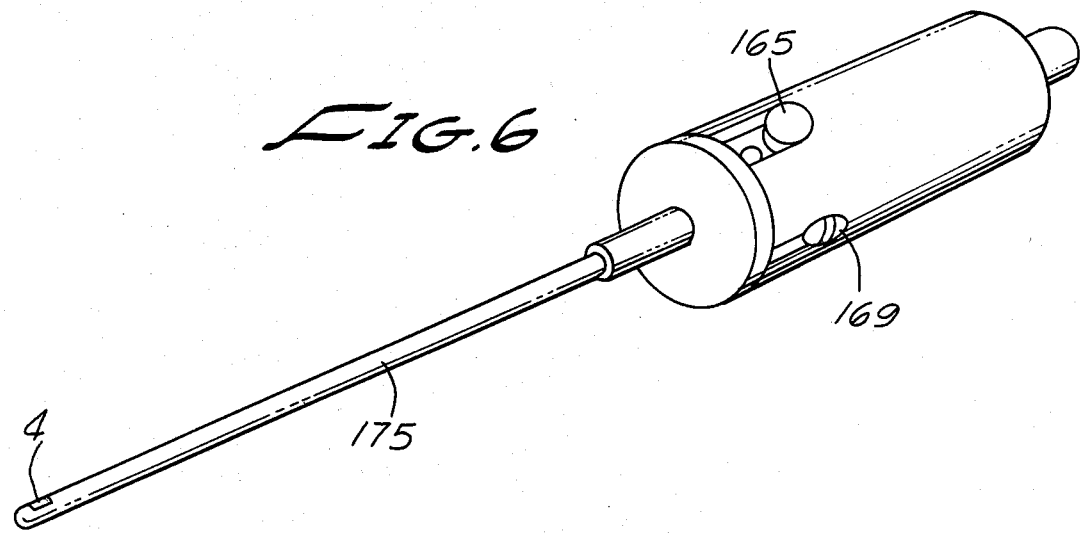
FIG. 6 is an enlarged view in perspective of a push-type surgical apparatus of this invention.
Figure 7:
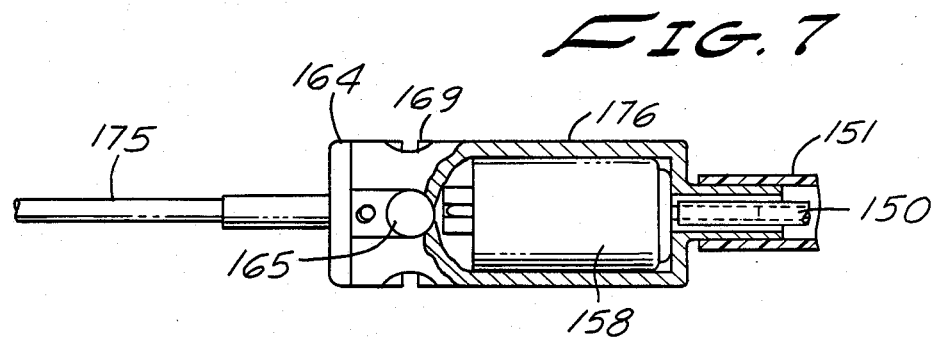
FIG. 7 is a fragmentary, sectional view of the handle portion of the device shown in FIG. 6.

Another form of the device of this invention is the push-type cutting embodiment shown in FIGS. 6 and 7. Certain parts of this embodiment provided in housing 176 are the same as the corresponding parts provided in the housing of the pulltype device shown in FIGS. 4 and 5. The embodiment shown in FIGS. 6 and 7 differs from that shown in FIGS. 4 and 5. Outer sleeve 175, which is fixedly attached to cap 164, is provided with an inner sleeve which has its end tapered and honed, in part, to a sharp cutting edge. Outer sleeve 175 is provided with a port 4 at the outer end portion thereof which is tapered and honed, in part, to a sharp edge, so that when inner sleeve 177 moves outwardly, the sharp cutting edges cooperate to shear off any vitreous or other material that has been sucked into the sleeve.

FIGS. 8 and 9 show a preferred embodiment of the new apparatus for intraocular surgery, generally designated 1. This apparatus includes a first tube 2 of very small diameter, preferably about 0.8 to about 1.0 millimeters in diameter, with a port generally designated 3 near one end of tube 2. Port 3 comprises a tissue-shearing portion 4 and, toward the closed end of tube 2, a portion 5 of substantially smaller size than tissue-shearing portion 3. A second tube 6, concentric with first tube 2, fits snugly together with tube 2 and is slidable with respect to tube 2.

Tube 6 is hollow, and has, at its end 7, a sharp cutting edge portion 8 and a smooth edge portion 9.

Joined to second tube 6 are a source of vacuum and means for connecting the vacuum source to tube 6 for drawing eye tissue into tube 2 through port 3.

The apparatus also includes means for reciprocating tube 6 with respect to tube 3 so that the sharp cutting edge portion 8 of tube 6 can cross port 3 and shear eye tissues sucked into the port, or so that the size of the opening in port 3 can be varied and restricted, as desired, to smaller-sized portion 5.

When the opening in port 3 is restricted to the smaller-sized portion 5, apparatus 1 can be utilized effectively for pinpoint, precision aspiration of eye tissue without cutting or disturbing surrounding tissue.

Figure 10:
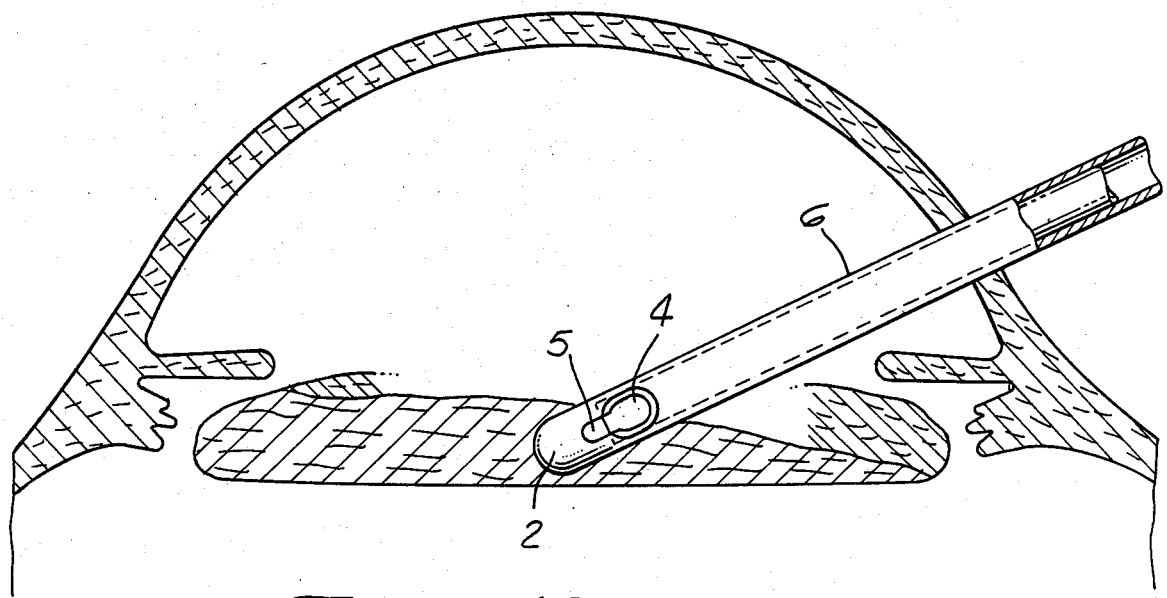
FIG. 10 illustrates the use of the new tool in the pinpoint, precision aspiration of eye tissue without cutting or disturbing other eye tissues.
Figure 11:
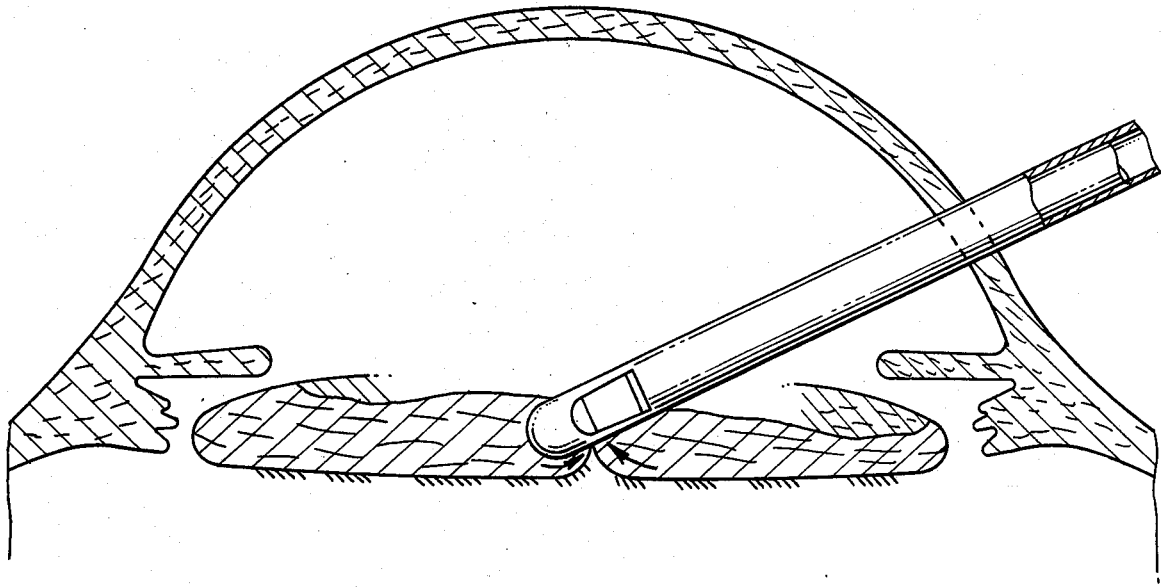
FIG. 11 illustrates the difficulties encountered in using the apparatus disclosed in the above-identified patents for aspiration of eye tissue without cutting.

FIG. 10 shows apparatus 1 with the opening in port 3 restricted to smaller-sized portion 5 for pinpoint, precision aspiration. As FIG. 11 shows, the ports in known apparatus of this kind can, and often do, withdraw or sever healthy eye tissue.

What is claimed is:

1. An apparatus for intraocular surgery such as removal or severing and removal of tissue from the eyeball of a patient, comprising a first tube of very small diameter having a port near one end thereof, said port comprising a tissue-shearing portion of a first, substantially uniform size and, toward the closed end of said first tube, a portion of a second substantially uniform, smaller size than said tissue-shearing portion, a second tube within said first tube, said tubes fitting snugly together and said second tube being slidable with respect to said first tube, said second tube being rotatable within said first tube, the end of said second tube adjacent said port having a sharp cutting edge portion and a smoother, substantially non-cutting edge portion, a source of vacuum, means for connecting said source of vacuum to the inner one of said tubes for drawing said tissue into the first tube through said port, and means reciprocating and rotating said second tube so that in one rotational orientation said sharp cutting edge portion can cross said port and cut tissue sucked into said port, in another rotational orientation the size of the opening in said port can be varied and restricted, without cutting as desired, to said second, substantially uniform, smaller sized portion.

2. An apparatus for intraocular surgery such as removal or severing and removal of tissue from the eyeball of a patient, comprising a first tube of very small diameter having a port near one end thereof, said port comprising a tissue-shearing portion of a first, substantially uniform size and, toward the closed end of said first tube, a portion of a second, substantially uniform, smaller size than said tissue-shearing portion, a second tube within said first tube, said tubes fitting snugly together and said second tube being slidable with respect to said first tube, said second tube being rotatable within said first tube, the end of said second tube adjacent said port having a sharp cutting edge portion and a smoother, substantially non-cutting edge portion, means connected to said tubes for drawing said tissue into said port, means for moving said one of said tubes so that in one rotational orientation said sharp cutting edge portion can cross said port and cut tissue sucked into said port, or so that in another rotational orientation the size of the opening in said port can be varied and restricted, as desired, and without cutting to said substantially smaller sized portion, a handle comprising a cylinder with a piston slidable therein, means connecting said second tube to said piston and pneumatic means for moving said piston back and forth in said first tube.

3. The apparatus of claim 2 wherein said pneumatic means comprises sources of air pressure and vacuum, and means alternately connecting said sources to the said cylinder for actuating said piston.

4. The apparatus of claim 2 wherein said pneumatic means includes a pair of small flexible hoses, one of which supplies pressure and vacuum from said sources, to actuate said piston, and the other of which is connected to the inner one of the cutting tubes for removal of tissue resulting from the cutting operation.

5. An apparpatus for intraocular surgery such as removal or severing and removal of tissue from the eyeball of a patient, comprising a first tube of very small diameter having a port near one end thereof, said port comprising a tissue-shearing portion of a first, substantially uniform size and, toward the closed end of said first tube, a portion of second substantially uniform, smaller size than said tissue-shearing portion, a second tube within said first tube, said tubes fitting snugly together and said second tube being slidable with respect to said first tube said second tube being rotatable within said first tube the end of said tube adjacent said port having a sharp cutting edge portion and a smooth, substantially non-cutting edge portion, and means reciprocating and rotating said second tube so that in one rotational orientation said sharp cutting edge portion can cross said port and cut tissue sucked into said port, or so that in one another rotational orientation the size of the opening in said port can be varied and restricted, as desired, and without cutting to said substantially smaller sized portion.

6. An apparatus for intraocular surgery for severing or removal of tissue from the eyeball of a patient, comprising a first tube of very small diameter having a port near one end thereof, and a second tube within said first tube, said tubes fitting snugly together and said second tube being slidable with respect to said first tube, said second tube rotatable within said first tube, the end of said tube adjacent said port having a sharp cutting edge portion and a smooth, substantially non-cutting edge portion, and means reciprocating said second tube so that in one rotational orientation said sharp cutting edge portion can cross said port and cut tissues sucked into said port, or so that in one rotational orientation the size of the opening in said port can be varied and restricted, as desired and without cutting.

* * * * *